(12) United States Patent
Meiss et al.

(10) Patent No.: US 8,312,779 B2
(45) Date of Patent: Nov. 20, 2012

(54) FORCE SENSOR FOR THE DETECTION OF A FORCE VECTOR

(76) Inventors: Thorsten Meiss, Darmstadt (DE);
Thorsten Kern, Alsbach-Hähnlein (DE);
Stephanie Sindlinger, Dieburg (DE);
Roland Werthschützky, Kleinmachnow (DE)

( * ) Notice: Subject to any disclaimer, the term of this patent is extended or adjusted under 35 U.S.C. 154(b) by 614 days.

(21) Appl. No.: 12/307,469

(22) PCT Filed: Jul. 6, 2007

(86) PCT No.: PCT/DE2007/001198
§ 371 (c)(1),
(2), (4) Date: Oct. 5, 2009

(87) PCT Pub. No.: WO2008/003307
PCT Pub. Date: Jan. 10, 2008

(65) Prior Publication Data
US 2010/0307265 A1    Dec. 9, 2010

(30) Foreign Application Priority Data
Jul. 6, 2006    (DE) .................... 10 2006 031 635

(51) Int. Cl.
*G01L 1/00*    (2006.01)
(52) U.S. Cl. .................................. 73/862.68
(58) Field of Classification Search ............ 73/862.68
See application file for complete search history.

(56) References Cited

U.S. PATENT DOCUMENTS

| | | |
|---|---|---|
| 3,261,204 A | 7/1966 | Jacobson |
| 4,299,130 A | 11/1981 | Koneval |
| 4,325,048 A | 4/1982 | Zaghi et al. |
| 4,331,035 A | 5/1982 | Eisele et al. |
| 4,718,287 A | 1/1988 | Mishliborsky |
| 4,748,858 A | 6/1988 | Ort |
| 4,787,256 A | 11/1988 | Cherbuy |
| 5,079,535 A | 1/1992 | Neuman et al. |
| 5,129,265 A | 7/1992 | Bartels et al. |
| 5,132,658 A * | 7/1992 | Dauenhauer et al. .......... 338/92 |

(Continued)

FOREIGN PATENT DOCUMENTS
DE    3940696 A1    6/1991
(Continued)

OTHER PUBLICATIONS

Beccai et al., "Silicon-Based Three Axial Force Sensor for Prosthetic Application", Proccedings of the 7th Italian Conference on Sensors and Microsystems, Feb. 4-6, 2002, pp. 250-255.

*Primary Examiner* — Lisa Caputo
*Assistant Examiner* — Octavia Davis-Hollington
(74) *Attorney, Agent, or Firm* — The Webb Law Firm (57) ABSTRACT

The invention makes it possible to determine a force vector that is applied to a tip of a minimally invasive surgical instrument. The force acts upon the housing, is directed to the base, and causes a deformation there in special beam structures. Said deformation is detected by tension-sensitive/extension-sensitive resistors whose changes are a measure for the applied force vector. The inventive measuring element comprises special mounting elements so as to be integrated into tube-type instruments such as guiding wires, fastening zones for additional components, an overload protection, and a head shape that is adapted to the treatment process.

15 Claims, 3 Drawing Sheets

U.S. PATENT DOCUMENTS

| | | | |
|---|---|---|---|
| 5,207,103 A * | 5/1993 | Wise et al. | 73/724 |
| 5,396,887 A | 3/1995 | Imran | |
| 5,522,266 A * | 6/1996 | Nicholson et al. | 73/708 |
| 5,988,000 A | 11/1999 | Adams | |
| 6,221,023 B1 | 4/2001 | Matsuba et al. | |
| 7,097,620 B2 * | 8/2006 | Corl et al. | 600/486 |
| 7,967,762 B2 * | 6/2011 | Corl et al. | 600/585 |
| 2010/0307265 A1 | 12/2010 | Werthschutzky et al. | |

FOREIGN PATENT DOCUMENTS

| | | |
|---|---|---|
| DE | 10319081 | 2/2004 |
| DE | 10303270 | 5/2004 |
| EP | 0176173 | 4/1986 |
| JP | 2006190050 | 7/1994 |
| JP | 2006064465 | 3/2006 |

\* cited by examiner

FORCE SENSOR FOR THE DETECTION OF A FORCE VECTOR

BACKGROUND OF THE INVENTION

1. Field of the Invention

The invention relates to a force sensor or a force sensor unit, in particular for an elongate device, and a method for measuring a force and its effective direction using the force sensor.

2. Description of Related Art

A particular application of this invention relates to catheter technology, determined by an elongate device for at least partial insertion into an organism through a body orifice. These elongate devices are used in particular in minimally invasive surgery and in the diagnosis of in particular human bodies. To ensure that, during the invasion by the elongate device, no body vessels are injured by the body-end tip of the elongate device which is usually operated manually by the treating medical practitioner, the medical practitioner necessarily orients himself according to the forces which are relayed to him by the handle of the elongate device. Due to friction and the inserted mass of the catheter or guide wire, which continuously increases during the course of the invasion of the catheter or guide wire in the body, the force relayed to the treating medical practitioner by the handle hardly provides any useful information regarding the forces which are actually occurring at the tip of the catheter or guide wire. So that the treating medical practitioner can impart the correct operating force on the handle of the catheter, extraordinary experience of operating catheters or guide wires is necessary.

DE 103 03 270 A1 discloses a catheter arrangement in which the force applied to the catheter tip during the insertion is measured. The corresponding force is relayed to the medical practitioner in a tactile fashion by means of a haptic handle. In particular for an inexperienced medical practitioner, this simplifies finding artery branches or perforations on the cardiac septum for example, and forms the basis of intuitive handling of the device. An electrodynamic drive apparatus using a measurement variable, representing the force at the tip, to generate haptic force pre-stressing is disclosed by DE 103 19 081 A1. The invention presented here makes it possible to measure the force at the tip of the elongate device and to evaluate the measurement signals, which is required for implementing the invention from DE 103 03 270 A1.

In accordance with U.S. Pat. No. 6,221,023 B1, provision is made for a force sensor at the tip of catheters which is based on a resistive functional operation. The force induced in the sensor is recorded by a resistor bridge circuit. The design of this sensor is complex due to the large number of parts, and the production and assembly costs associated with this mean that the known sensor is unsuitable for catheters in particular due to the preferred single-use property of the latter. Furthermore, the surface for the primary contacting of the measurement element is designed to be perpendicular to the longitudinal direction of the catheter, and hence the surface for contacting is limited by the diameter of the elongate device. It is for this reason, and due to the large number of parts, that miniaturization possibilities of the force sensor, in particular below a catheter diameter of less than 3 mm, can only be implemented with a very high design complexity. Due to the large dimensions, it is possible to conclude that the sensor completely closes off the catheter tube at the tip. However, this means that the functionality of the catheter tube, by means of which instruments and liquids are inserted into the body, is no longer given. Integrating the sensor into the substantially thinner guide wire required during catheterizations is not possible due to the large dimensions, the large number of parts and the inexpedient wire guide through the contact surface oriented perpendicularly to the longitudinal direction. JP 06190050 A describes a tactile sensor which can be attached to the outer wall of catheters. It is proposed to produce this sensor from a very thin silicon disk. However, it is not possible for very thin elements to record the occurring forces in the region of approximately 300 mN. The use of thicker, more stable silicon disks can be discarded, since bending thicker disks, which is required for integration into the device, would lead to the material breaking.

"Beccai L et al.: Silicon-based three axial Force Sensor for Prosthetic Applications, Sensors and Microsystems, Proceedings of the 7th Italian Conference 2002" present a force sensor which is intended to be integrated into leg prostheses. The force vector can be determined by measuring the direction and magnitude of the force. Resistive elements, which are not interconnected to form a Wheatstone bridge, are used to measure the forces. However, bridge interconnections which can attain high measurement accuracy are sought after for the integration into an elongate device because in this case the signals can be transmitted almost independently of the feed line resistances in the long, thin feed lines. Otherwise the measurement signal depends on the temperature of the feed line, and hence on the insertion length of the device, particularly in the case of long devices inserted into the body. The production of the elements requires a two-sided, multistage dry etching process. Nevertheless, the measurement element must still be mounted over a special counter body to make a deflection of the measurement beams possible. The sensor thus comprises at least two parts which have to be connected accurately to one another. The exposed force detector, referred to as a mesa, is designed to have a long length; it approximately has a length which corresponds to the thickness of the original material to be precise. Hence this sensor always has, due to its operating principles, both a very much increased measurement sensitivity and susceptibility to destruction toward lateral forces compared to the force applied along the longitudinal direction. This is inexpedient because it is desirable in particular to measure the forces in the longitudinal direction of the device, or to obtain a balanced sensitivity for different force components. The measurement element has a plane of electrical contacts which is perpendicular to the longitudinal direction, and so the contacting surface on the diameter of the installation area is limited, which makes contacting more difficult. The measurement element has a diameter of approximately 1 mm, which is large compared to guide wires, so integration into the guide wire is impossible. This shows that the prior art relating to tactile sensors for integration into catheters and guide wires does not conform to the imposed requirements with respect to miniaturization, high stability, simple production and low costs.

SUMMARY OF THE INVENTION

It is an object of the invention to specify a force sensor of the abovementioned type which has a simple design and is composed of one part which can be integrated into elongate devices having a diameter of less than 3 mm, preferably of less than 0.33 mm (1 French), and which force sensor can detect forces which at least in part act on the longitudinal direction of the elongate device so that a force-dependent torque is imparted on the user, if possible by detecting the force vector applied to the guide wire tip, i.e. determining the magnitude of the force in three independent directions, and conclusions with regard to the direction of the acting force are also possible, so that forces can be determined according to magnitude and direction.

Accordingly, the force sensor according to the invention is designed to detect a force which acts on an elongate device, in particular an elongate medical device such as a catheter or a guide wire, with it being possible for said force to have a non-negligible force component in the longitudinal direction of the elongate device. The sensor according to the invention has a force detector by means of which at least a substantial amount of the force to be detected can be induced, in a targeted fashion, either directly into the sensor or via the elongate device. According to the invention, the sensor is designed such that it can be attached to the elongate device and can in particular be retrofitted to already existing elongate devices. The option of simple miniaturization of the force sensors makes it possible to integrate the force sensors both into the catheter wall, without closing off the distal catheter opening, and into the guide wire, which is particularly important and challenging. Centering elements and assembly stops are provided to assemble the sensor on a guide wire so as to be able to realize the assembly, which constitutes a great challenge in miniaturized systems, in a simple and cost-effective fashion. The magnitude of the forces on the elongate device and moreover the direction in which they act can be determined by particular design features.

In particular, the force sensor according to the invention offers the following advantages over the mentioned, known force sensors:

- the sensor according to the invention affords the possibility of integrating a force sensor system into elongate devices which have a lateral extent or a diameter of less than 3 mm, in particular of less than 0.33 mm (1 French);
- the sensor according to the invention is composed of one part; for this reason and due to disk connection production technology, it is particularly suitable for mass production. The production costs are very low, there are no applicable assembly costs for the sensor element itself, and assembly on the elongate device is particularly simple;
- the special design and monolithic integration of assembly elements make it possible to assemble the very small force sensors on the guide wire in a simple manner;
- the integration of mechanical stops prevents the sensor from being destroyed when overloaded;
- the particular design and mechanical stiffness of the force sensor associated therewith make the housing very simple, thin and cost-effective by either casting or coating. Thus, the force sensor readily satisfies the stringent hygiene requirements of medicine technology;
- the shape of the head of the sensor according to the invention can have a very variable design, as a result of which matching to different catheterization treatment scenarios is possible;
- the sensor according to the invention can obtain very high-resolution force magnitude and direction measurements due to use of the piezoresistive principle of operation while using cost-effective external evaluation electronics;
- the sensor according to the invention can effect particularly precise measurements because silicon can preferably be used as a basic material so that in the case of force loading and unloading, the output signal in particular reproduces the applied force;
- the sensor according to the invention can undergo miniaturization far below the required lateral dimensions of 0.3 mm using currently available technology;
- additional electronics can easily be integrated monolithically in the sensor according to the invention so that perturbations in the signal transmission, but also in particular the number of electrical supply lines required, can be reduced to a minimum. The already present components of the elongate device can be used for energy and signal transmission, as a result of which the costs of the overall device are increased only very slightly by integrating the force sensor.

The sensor according to the invention can detect the magnitude and/or effective direction of forces in real time and, in particular, continuously. In particular, the sensor according to the invention is designed to detect a force mainly in the longitudinal direction of the elongate device.

The sensor according to the invention is constructed from a basic element which deforms as a function of the applied force. This deformation generates mechanical stresses which are detected by the characterized measurement beam by means of stress- and stretch-sensitive resistors. The change in these measured resistances is proportional to the applied force.

In the horizontal measurement beam, a force $F_z$ coupled into the axial direction generates tensile stresses in the vicinity of the top side, and compressive stresses in the vicinity of the beam underside. These mechanical stresses effect opposite changes in the resistance in the resistors doped into the beam, which changes can be measured by means of a Wheatstone bridge interconnection, for example. The change in the resistance or the bridge output voltage thus is a measure of the applied force $F_z$.

Further resistors can be inserted into or attached to a measurement beam aligned with the axial direction of the elongate device. Lateral forces acting on the head structure effect a deformation of the beam, which effects mechanical stresses. These mechanical stresses can be determined using resistors and are a measure of the acting lateral forces.

The forces applied to the sensor lead to deformations of the mechanical structures. Monolithically integrated, mechanical overload stops in the sensor according to the invention make it possible to prevent very large deformations of the geometry and hence prevent a destruction of the force sensor in the case of excessively large loads. The integration can be effected without additional process steps; a counter body to limit the deformation is not required.

Elements to simplify assembling the sensor on the guide wire are preferably integrated into the sensor according to the invention. For example, to this end, provision is made for a stand which affords the possibility of easily inserting the base body into the cavity opening of the guide wire by tapering toward the bottom end. Moreover, provision can be made for attachment elements for further components of the guide wire, in particular a securing band and a wire core. This is made possible, for example, by means of an incision at the lower end of the stand.

All embodiments can be produced by means of a microproduction method, preferably by means of volume-micromachinery in silicon. In the process, a silicon disk is structured such that resistors are generated by inserting a dopant in the silicon, the magnitude of their resistances changing as a function of the mechanical stress. Due to the electrical action between the silicon disk and the dopant, these resistors are only electrically connected in the desired regions; otherwise they are isolated from each other by the formation of a pn-transition as a result of the selected design. As a rule, these resistors are attached to the top side of the measurement element and not in recesses in the silicon disk because this is easier to produce. By way of example, the measurement elements can be produced in the following manner (workflow without cleaning steps):
- structuring the resistors,
- opening the contact regions,
- structuring the printed circuit board tracks,
- etching the mechanical structure while simultaneously decollating, e.g. by dry etching.

The production of the elements only has few process steps compared to the prior art. This is due to the fact that there is no need for a sawing process to decollate the measurement elements. Furthermore, no counter body is required to ensure the deformation of the body; connecting said counter body to the base body would require another process step. The resistors can be passivated during doping in the case of a suitable selection of the process parameters and hence this does not constitute another process step either. Overall, the production of the measurement element only requires four mask layers. The methods of microstructuring afford the possibility of simultaneously producing a particularly large number of sensors on one disk (batch method, profitable production) and thus make very cost-effective measurement elements possible.

In addition to the embodiment as a miniaturized piezoresistive measurement element, in general it is also possible to design the presented measurement elements macroscopically, and use a strain gauge or thick-film resistors or thin-film resistors to measure the stress or stretching.

By way of example, it is possible to use the sensors at the tip of guide wires, or else at an arbitrary position in the catheter.

BRIEF DESCRIPTION OF THE DRAWINGS

In the following text the invention will be explained in more detail on the basis of exemplary embodiments with reference to the drawing, in which.

DETAILED DESCRIPTION OF THE INVENTION

It can be seen from the drawing that the sensor according to the invention is designed monolithically from a base body (100) which deforms as a function of the applied force. This deformation generates mechanical stresses which are detected on the measurement beams (101a and b, 102a and b) by means of stress- or stretching-sensitive resistors. The change in these measurement resistors is proportional to the applied force.

In the horizontal measurement beams (101a and b), a force $F_z$ coupled into the axial direction generates tensile stresses in the vicinity of the beam top side and compressive stresses in the vicinity of the beam underside. These mechanical stresses effect changes in the resistance in the same or opposite sense in the resistors $R_1$ to $R_4$ doped into the beam, which changes can be measured by means of a Wheatstone bridge interconnection, for example. Hence, the change in the resistance or the bridge output voltage is a measure of the applied force $F_z$.

The resistors are preferably arranged in the form of a Wheatstone bridge circuit. This ensures stable measurements. If the resistors are interconnected to form a Wheatstone bridge, the output signal for one force component is maximized, e.g. when $F_z$ is applied, whereas said output signal is minimized when the force component $F_y$ is applied. By interchanging the supply and signal lines of the electronics for example, the sensitivity of the resistor interconnection on the measurement beam can be maximized for one force component and simultaneously be minimized for the other force component. This makes it possible to precisely and independently determine the magnitude and direction of the applied force components $F_z$ and $F_y$. Thus, quasi-continuous determination of the force components $F_z$ and $F_y$ is possible by temporally rapid switching of the force sensor contacts.

The beam structure (106) is very suitable for measuring lateral forces $F_x$ and $F_y$ acting on it. A force $F_x$ acting on the front surface (105) leads to a stretching in the longitudinal direction of resistors on the measurement beam, and hence to an increase in the resistance of resistors arranged in the longitudinal direction. Although a single resistor is sufficient to determine the force component $F_x$, using the piezoresistive principle can obtain changes in the resistance in the opposite sense by arranging resistors along and across the beam (106), and hence voltage dividers or bridge circuits can be integrated to increase the measurement accuracy. In the beam (106), a force $F_y$ causes tensile stresses on the right-hand side, and compressive stresses on the left-hand side. This mechanical stress can be measured by at least one piezoresistive resistor. Preferably, two resistors which are inserted adjacent to one another in a vertical fashion are used, and they can be interconnected to form a voltage divider. Whereas the force $F_y$ causes an opposing change in the resistance of the two resistors aligned vertically next to one another, a force $F_x$ causes a change in the same sense in the resistance of the two resistors. If the resistors are interconnected to form a voltage divider, the overall resistance of the voltage divider increases, and thus it is a measure for the force $F_x$. Hence, the difference of the change in the resistance is a measure of the force $F_y$, and the size of the change in the resistance in the same sense is a measure of the force $F_x$. Due to the small dimensions of the force sensor, the use of piezoresistive Hall elements is also expedient. In the case of moderate miniaturization, the interconnection of a plurality of resistors to form one or more full bridges on the beam (106) can improve the measurement accuracy. In the case of a very high degree of miniaturization, it can be expedient to only integrate a single resistor in the center of the beam (106). Then the deformation in the x-direction can be determined by the increase of the individual resistance, or by the increase of the overall resistance in the case of a series circuit with further resistors. However, a lateral deformation in the y-direction, and hence the force $F_y$, cannot be measured by this resistor. If the force component $F_y$ is nevertheless intended to be detected, it can be detected, as described above, by means of the resistor arrangement on the measurement beam (101), for example by exchanging the supply and signal lines.

There are many possibilities for measuring mechanical stresses, from which the forces $F_x$, $F_y$ and $F_z$ can be determined, by different resistor arrangements. In order to obtain functions of the change in the resistance which are as independent of the individual force components as possible, further resistor arrangements are feasible, such as using horizontally oriented resistors arranged to form voltage dividers or bridge circuits or piezoresistive Hall elements. Mechanical tensile and compressive stresses, which are suitable for measuring the forces by means of resistors, also occur in the vertical beam structure (102) and in the head structure (103). In the case of a high degree of miniaturization, this affords the advantageous possibility of implementing a full bridge structure without having to arrange directly next to one another resistors which have the required opposing resistor arrangement. Hence, the remaining space on a measurement beam can be used for electric printed circuit board tracks. This also makes it possible to further decrease the thickness of the measurement beam (101) and hence make it possible to measure even smaller forces.

Figure 1A:
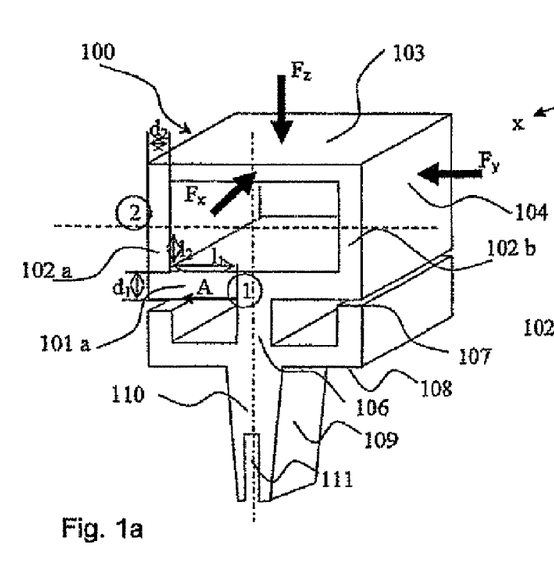
FIG. 1a shows, for the purposes of clarifying mathematical contexts, a schematic diagram of the sensor according to the invention, the head of which has a symmetric, rectangular design.

Moreover, in the case of the sensor according to the invention, it is easily possible in a number of ways to limit the deflection of the beam (101) and the tipping of the beam (106) by using a mechanical stop (107). Thus, an overload protection can be implemented. This overload protection can be implemented by a simple stop, as shown in FIG. 1*a*. Alternative arrangements, for example integration between the end surface (103) and measurement beam (106), are also feasible. The design of the overload protection should be matched to the possible gap widths and possible aspect ratios of the production process.

FIG. 1*a* furthermore shows a stand region which tapers toward the bottom end of the base body. This makes it easier to assemble the force sensor on the guide wire.

Figure 1B:
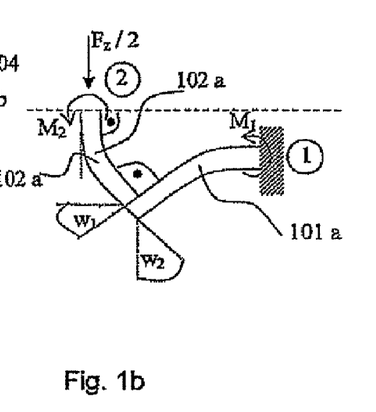
FIG. 1b shows a detail of the schematic diagram 1a which clarifies the bending angles and bending moments on a vertical beam for calculating the mechanical stresses in the case of an axially induced force by the force $F_z$.

FIG. 1*b* shows a detail from the measurement beam (101*a*). What is shown is that a deformation of the measurement beam (101*a*) is set when a force $F_z$ is coupled into the force sensor. This deformation in turn causes a deformation of the left vertical measurement beam (102*a*), as a result of which a moment $M_1$ applied to the measurement beam (101*a*) is decreased, and the measurement effect is reduced. The overall head structure of the force sensor therefore also needs to be taken into account when optimizing the sensor.

Figure 2:
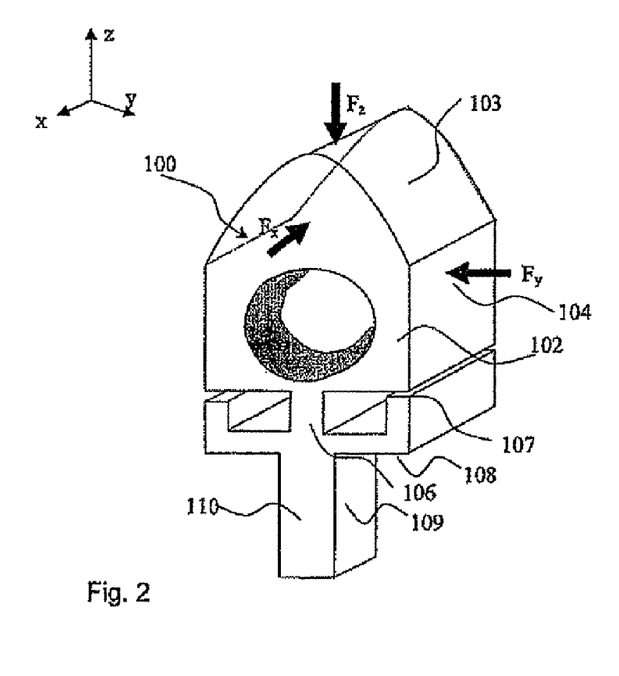
FIG. 2 shows an embodiment with a head having a rounded shape, and with the recess for generating the beam structure not being designed perpendicularly.

FIG. 2 shows another embodiment of the force sensor according to the invention. In this case, the end surface (103) is designed to be rounded off. The rounding off can be advantageous for designing the distal end of the elongate device such that, as far as possible, there are no injuries to the patient during use. However, it can also be designed with a tip or cutter in order to be able, for example, to pass more easily through constrictions, occlusions or tissue, or to couple forces into the force sensor in a more reproducible fashion. Moreover, the beam structure in FIG. 2 is generated by introducing a hole.

Figure 3:
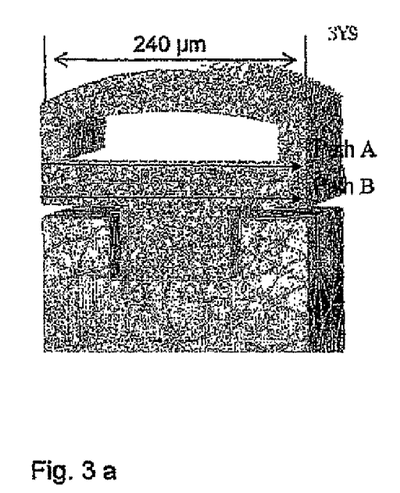
FIG. 3a shows a geometric model of a preferred exemplary embodiment for calculating the mechanical stresses and changes in the electrical resistance using the finite element method (FEM) in the case of a force induced from all three spatial directions.
FIG. 3b shows the change in the resistance for resistors attached along path A and path B for a force of 100 mN induced into the sensor end surface 103 along the axial direction ($F_z$), as determined by the FEM simulation.

FIG. 3*a* shows a geometric model of a preferred force sensor according to the invention for calculating mechanical stresses and changes in the electrical resistance with the aid of the finite element method (FEM), with forces being induced from all three spatial directions. The mechanical stresses are calculated along path A and path B and the changes in resistance of the resistors are calculated via mathematical descriptions of the piezoresistive effect. FIG. 3*b* shows the change in the resistance; effective resistance changes of between 0.5% and 1.5% can be expected in the case of a nominal load of $F_z$=100 mN.

Figure 4:
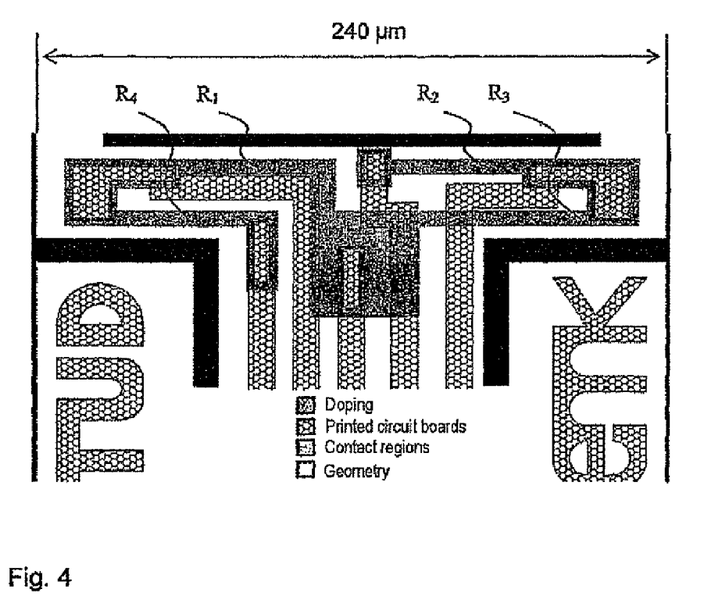
FIG. 4 shows a possible layout for the electrical structure of a sensor.

FIG. 4 shows, in an exemplary manner, a possible layout for the electrical structure of a sensor according to the invention. In this case, resistors are only doped into the vertical measurement beam (101*a* and *b*) and interconnected as a Wheatstone bridge.

Figure 5:
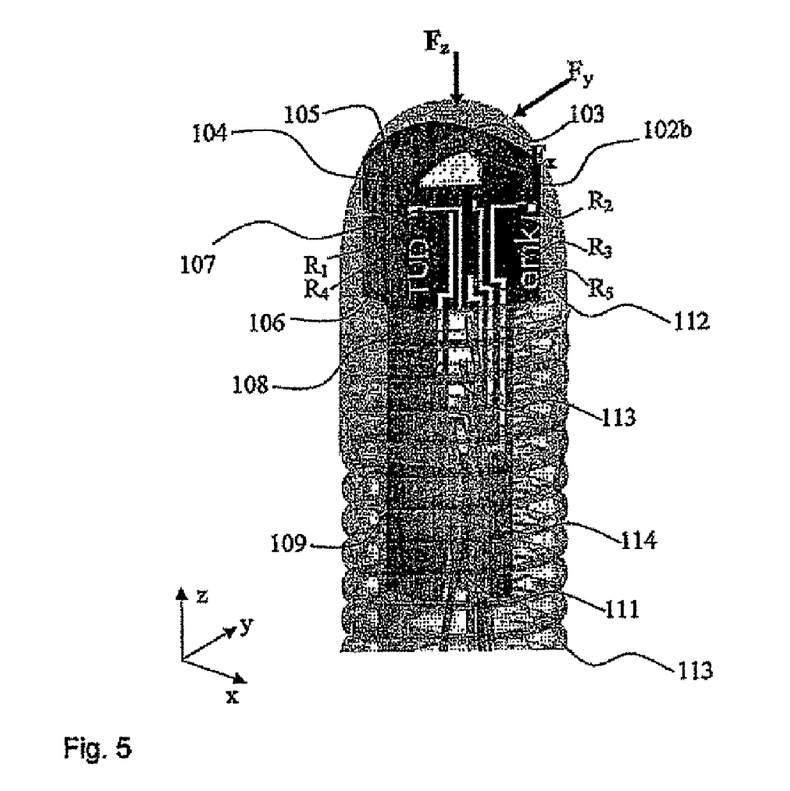
FIG. 5 shows a CAD drawing of a built force sensor assembled on a guide wire.

FIG. 5 illustrates an electrically contacted sensor which is integrated into the tip of a guide wire. It is housed by being encapsulated by a relatively soft, biocompatible material such as silicon or polyurethane. The high stiffness of the measurement element compared to the housing material ensures a low influence of the housing on the measurement signal. The semitransparent display makes it possible to see the contact surfaces and connection lines.

Figure 6:
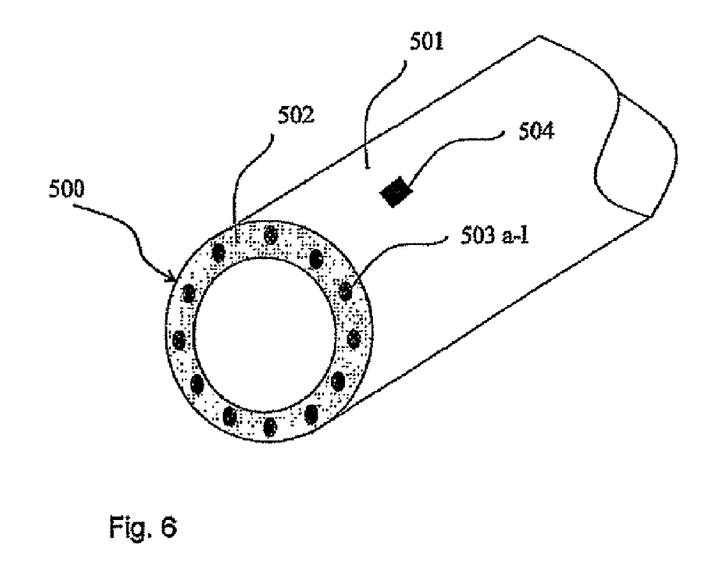
FIG. 6 shows a schematic diagram of a cut in the vicinity of the front surface of a catheter with integrated force sensors.

As shown in FIG. 6, it is also possible to integrate the force sensors at arbitrary locations within or on catheter tubes due to the small dimensions of said sensors. It is also possible to integrate a number of force sensors in a catheter wall. This makes it possible to record spatially resolved force profiles. The distal opening of the catheter is completely preserved due to the high degree of miniaturization of the sensors. The force sensors according to the invention are preferably integrated in or attached to the distal end of the elongate device, or else at an arbitrary location on or in the elongate device.

It is also possible to house evaluation electronics directly on or attached to the measurement element. By way of example, this can be advantageous in that an increased signal voltage is generated by pre-amplification. This increases the signal-to-noise ratio (SNR), and hence the resolution as well. In the case of integrated electronics, it is possible to transmit the signals with little influence from the feed line by means of a coded or modulated transmission of the signals or by a voltage-proportional current conversion. A constant voltage feed can be implemented by integrating constant voltage sources so that the resolution of lateral force components is increased without the line resistance having a noticeable effect on the measurement result. Furthermore, integrated electronics make it possible to directly measure electrical difference voltages on the resistors and hence make it possible to very precisely determine the direction and magnitude of the forces. Integrated electronics can effect potential matching of the signals on the chip, and electrical difference voltages can be related to individual ground lines. As a result of this, electrical lines can be dispensed with. As a result of this, the assembly complexity and hence the production costs of the entire device are reduced. Moreover, the spatial requirements of the lines are reduced, making further miniaturization of the diameter of the elongate device possible. Modulating the signals in primary electronics integrated in the measurement element makes it possible to reduce the number of lines to two, and in particular to one line. Transmitting energy and signals wirelessly is also possible by integrating a wireless transmission unit.

The features of the invention disclosed in the preceding description, in the drawings and in the claims can be essential, both on their own and in arbitrary combinations, for realizing the invention in its different embodiments.

LIST OF REFERENCE SYMBOLS

100 Base body
101*a* Left horizontal measurement beam
101*b* Right horizontal measurement beam
102*a* Left vertical measurement beam
102*b* Right vertical measurement beam 103 End surface, force applied from the axial direction ($F_z$)
104 Left surface, force applied from the y-direction ($F_y$)
105 Front surface, force applied from the x-direction ($F_x$)
106 Vertical measurement beam to measure radially applied forces ($F_x$, $F_y$)
107 Mechanical stop as overload protection
108 Mechanical stop as an assembly aid
109 Beam for housing contact surfaces, for attaching the measurement element and for centering in the guide wire during the assembly
110 Surface for bonding contacts
111 Incision for affixing a guide wire core and a securing band
112 Housing
113 Guide wire coil
114 Energy and signal lines
$R_1 \ldots R_5$ Electrical resistors which change their basic resistance on the basis of mechanical stretching and stress
$F_z$ Force component of the z-direction, axial, force component applied to the wire in the longitudinal direction
$F_x$ Force component from the x-direction
$F_y$ Force component from the y-direction
F Force vector, comprising the force components $F_z$, $F_x$ and $F_y$
500 Catheter tube with integrated force sensors
501 Outer cladding of the catheter
502 Front end of the catheter
503 Force sensors for recording the forces at the tip of the catheter
504 Force sensors for recording the forces at an arbitrary place on/in the catheter

The invention claimed is:

1. A force sensor for detecting a force vector applied to an elongate device, the force vector comprising a non-negligible force component along the longitudinal direction of the elongate device, wherein the force sensor comprises:
 a base body of monolithic construction having an end surface for receiving the force vector;
 one or more stress/stretching-sensitive resistors, wherein the one or more resistors are arranged on beam structures bounded by incisions, wherein the edges thereof form substantially perpendicular angles with the end surface of the base body;
 an energy and signal line to a measurement region of the force component $F_z$ effected over a region axially aligned with respect to the elongate device, wherein the region is narrower than the maximum width of the end surface of the base body;
 electrical connection surfaces attached non-perpendicularly to the axial direction of the elongate device; and
 a connection region including an assembly stop.

2. The force sensor as claimed in claim 1, wherein the force sensor is further configured to measure at least one applied lateral force component $F_x$ or $F_y$.

3. The force sensor as claimed in claim 2, wherein the one or more resistors are arranged on a front side of the base body.

4. The force sensor as claimed in claim 3, wherein the resistors are one of doped, thin-film resistors or thick-film resistors, or a strain gauge.

5. The force sensor as claimed in claim 4, further comprising at least one resistor for each force component to be measured.

6. The force sensor as claimed in claim 4, wherein the region axially aligned with respect to the elongate device is a vertical measurement beam.

7. The force sensor as claimed in claim 6, wherein one of the resistors is arranged in the center of the vertical measurement beam.

8. The force sensor as claimed in claim 6, wherein two resistors are arranged opposite one another in an area of the outer edge of the vertical measurement beam.

9. The force sensor as claimed in claim 4, wherein the one or more resistors are at least in part interconnected to form Wheatstone bridge circuits.

10. The force sensor as claimed in claim 9, wherein the bridge circuits are in an open or closed configuration.

11. The force sensor as claimed in claim 1, wherein the end surface is planar or round.

12. The force sensor as claimed in claim 1, wherein the assembly stop is configured to limit the force-dependent deformation of the force sensor.

13. The force sensor as claimed in claim 1, further having integrated therein an electronic arrangement for signal processing, power feeding, or data transmission.

14. The force sensor as claimed in claim 1, wherein the elongate device is a catheter or a guide wire.

15. The force sensor as claimed in claim 1, wherein the end surface is adapted to receive a tip or cutter.

* * * * *

UNITED STATES PATENT AND TRADEMARK OFFICE
CERTIFICATE OF CORRECTION

PATENT NO. : 8,312,779 B2
APPLICATION NO. : 12/307469
DATED : November 20, 2012
INVENTOR(S) : Meiss et al.

Page 1 of 1

It is certified that error appears in the above-identified patent and that said Letters Patent is hereby corrected as shown below:

Title Page, item (56);

Column 2, OTHER PUBLICATIONS, delete "Proccedings" and insert
-- Proceedings --

Signed and Sealed this
Nineteenth Day of March, 2013

Teresa Stanek Rea
*Acting Director of the United States Patent and Trademark Office*